(12) United States Patent
Wang et al.

(10) Patent No.: US 10,590,088 B2
(45) Date of Patent: *Mar. 17, 2020

(54) 4-(BENZIMIDAZOL-2-YLAMINO)BENZAMIDE DERIVATIVES AND METHODS OF SYNTHESIS THEREOF

(71) Applicant: TRANSLATIONAL DRUG DEVELOPMENT, LLC, Scottsdale, AZ (US)

(72) Inventors: Tong Wang, Scottsdale, AZ (US); Stephen Gately, Scottsdale, AZ (US)

(73) Assignee: Translational Drug Development, LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,926

(22) Filed: Oct. 16, 2018

(65) Prior Publication Data

US 2019/0084940 A1 Mar. 21, 2019

Related U.S. Application Data

(63) Continuation-in-part of application No. 15/245,166, filed on Aug. 23, 2016, now abandoned, which is a continuation of application No. 14/733,952, filed on Jun. 8, 2015, now Pat. No. 9,464,059, which is a continuation of application No. 13/380,213, filed as application No. PCT/US2010/038290 on Jun. 11, 2010, now Pat. No. 9,125,901.

(60) Provisional application No. 61/219,681, filed on Jun. 23, 2009.

(51) Int. Cl.
| | |
|---|---|
| *C07D 235/30* | (2006.01) |
| *C07D 401/04* | (2006.01) |
| *C07D 403/04* | (2006.01) |
| *A61K 31/415* | (2006.01) |

(52) U.S. Cl.
CPC .......... *C07D 235/30* (2013.01); *A61K 31/415* (2013.01); *C07D 401/04* (2013.01); *C07D 403/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,125,901 | B2 * | 9/2015 | Wang | A61K 31/415 |
| 9,464,059 | B2 * | 10/2016 | Wang | A61K 31/415 |
| 2005/0065179 | A1 * | 3/2005 | Poitout | C07D 235/30 |
| | | | | 514/303 |

OTHER PUBLICATIONS

Nofal et al. (Arch. Pharm. Res., vol. 25, No. 3, pp. 250-257 (2002).*

* cited by examiner

*Primary Examiner* — Valerie Rodriguez-Garcia
(74) *Attorney, Agent, or Firm* — Rodney J. Fuller; Booth Udall Fuller, PLC

(57) ABSTRACT

Disclosed are 4-(benzimidazol-2-ylamino)benzamide derivatives useful in slowing the expansion of cancer cells and methods of synthesizing derivatives of formula 5 or formula 7:

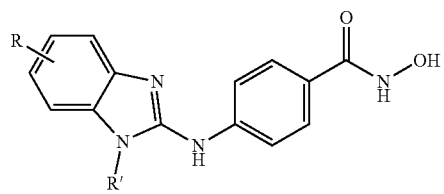

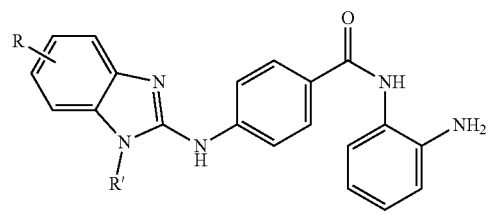

wherein R and R' are defined herein.

17 Claims, 1 Drawing Sheet

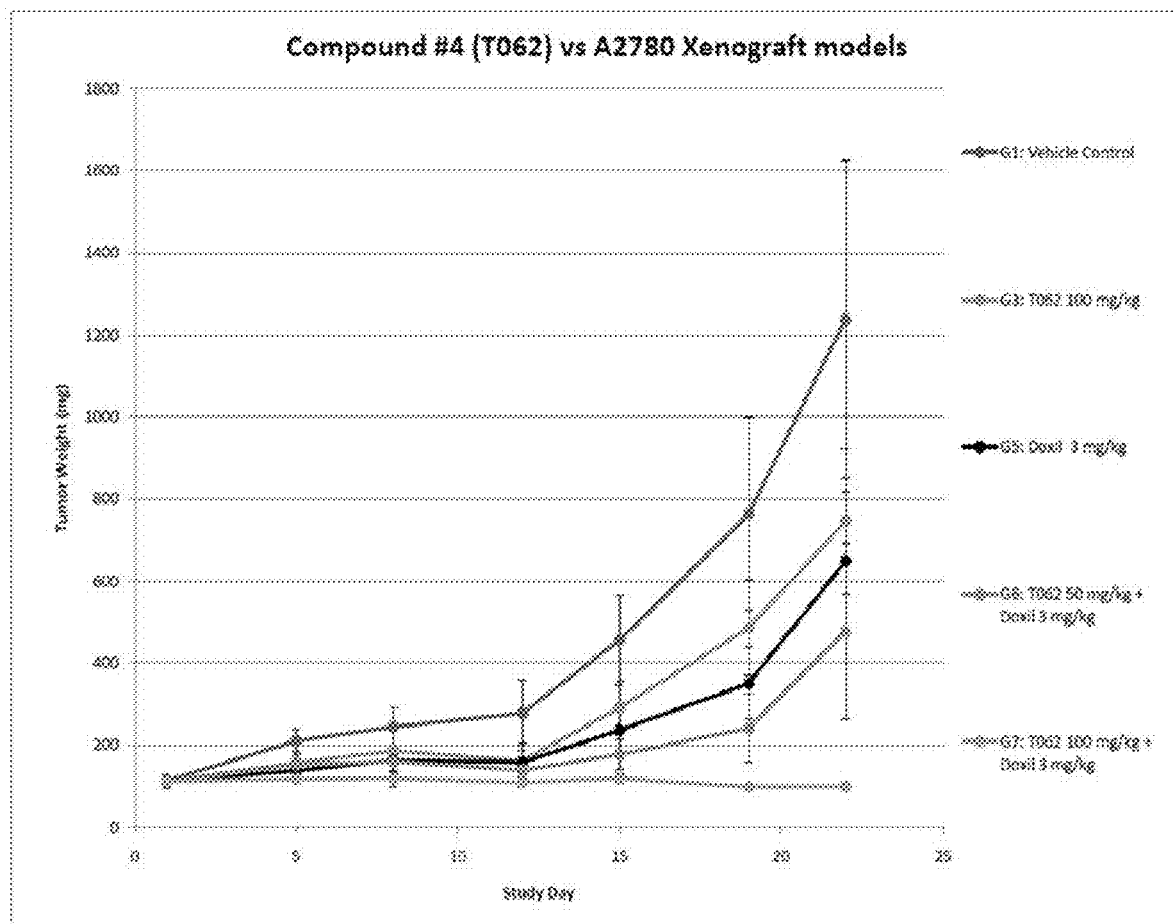

4-(BENZIMIDAZOL-2-YLAMINO)BENZAMIDE DERIVATIVES AND METHODS OF SYNTHESIS THEREOF

CROSS-REFERENCE TO RELATED PATENT APPLICATION

This application is a continuation-in-part of U.S. patent application Ser. No. 15/245,166, filed Aug. 23, 2016 (published as US 20160362382), which is a continuation of U.S. patent application Ser. No. 14/733,952, filed Jun. 8, 2015 (now U.S. Pat. No. 9,464,059) which is a continuation of U.S. patent application Ser. No. 13/380,213, filed Feb. 22, 2012 (now U.S. Pat. No. 9,125,901), which is the U.S. National Stage of International Application No. PCT/US2010/038290, filed Jun. 11, 2010, which claims the benefit of U.S. Provisional Patent Application No. 61/219,681, filed Jun. 23, 2009, the contents of each of which are incorporated by reference in their entireties for all purposes.

BACKGROUND OF THE INVENTION

Cancer is the second leading cause of death in the United States and despite new breakthroughs that have led to decreased mortality, many cancers remain refractory to treatment. Additionally, typical treatments such as chemotherapy, radiotherapy and surgery cause a broad spectrum of undesirable side effects. In addition, many cancers often develop resistance to current chemotherapies over time. Clearly the field is in significant need of novel compounds and methods of slowing the expansion of cancer cells and that are useful in the treatment of cancer.

BRIEF SUMMARY OF THE INVENTION

The present invention provides among other things a compound that is effective in the treatment of cancer.

It is an object of the invention to provide a pharmaceutical composition that slows the expansion of cancer cells.

It is an object of the invention to treat various forms of cancer.

The above and other objects may be achieved using devices involving a compound of formula

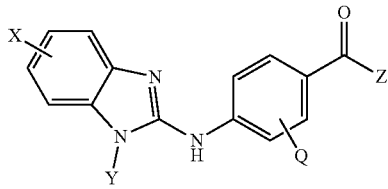

The group denoted by X may be any of H, halo, —$C_1$-$C_6$ alkyl, aryl, —$C_3$-$C_7$ cycloalkyl or -3-to 10-membered heterocycle, any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR', wherein R' may be —H or —$C_1$-$C_6$ alkyl.

The group denoted by Y may be any of H, —$C_1$-$C_6$ alkyl, —$C_3$-$C_7$ cycloalkyl, any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R)$_2$, —NHC(O)R' or —C(O)NHR' groups wherein R' may be —H or —$C_1$-$C_6$ alkyl.

The group denoted by Z may be methyl, —NH2, —NHOH, or phenylene diamine group (II)

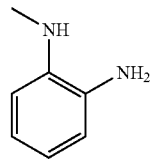

The group denoted by Q may be H, F or Cl.

The above and other objects may be achieved by methods involving slowing the growth of tumors with an effective amount of a pharmaceutical composition that includes the disclosed compound and, in some aspects of the invention, one or more pharmaceutically acceptable carriers.

The above and other objects may be achieved by methods involving treating a mammal with an effective amount of a pharmaceutical composition that includes the disclosed compound and, in some aspects of the invention, one or more pharmaceutically acceptable carriers.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. Inventors are fully aware that they can be their own lexicographers if desired.

BRIEF DESCRIPTION OF THE FIGURE

FIG. 1 depicts in vivo efficacy studies of compound #4 (N-hydroxy-4-(1-(2-methoxyethyl)-1H-benzo[d]imidazol-2-ylamino)benzamide) in A2780 xenograft models.

DETAILED DESCRIPTION OF THE INVENTION

Herein the Inventors disclose a compound with a formula of:

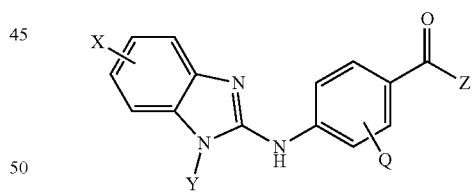

The group denoted by X may be any of H, halo, —$C_1$-$C_6$ alkyl, aryl, —$C_3$-$C_7$ cycloalkyl or -3- to 10-membered heterocycle, any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or —$C_1$-$C_6$ alkyl.

The group denoted by Y may be any of H, —$C_1$-$C_6$ alkyl, —$C_3$-$C_7$ cycloalkyl, any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' wherein R' may be —H or —$C_1$-$C_6$ alkyl.

The group denoted by Z may be methyl, —NH2, —NHOH, or phenylene diamine group (II).

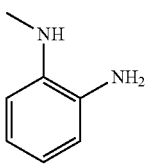

The group denoted by Q may be H, F or Cl.

A —$C_1$-$C_6$ alkyl group includes any straight or branched, saturated or unsaturated, substituted or unsubstituted hydrocarbon comprised of between one and six carbon atoms. Examples of —$C_1$-$C_6$ alkyl groups include, but are not limited to methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl groups. Substituted —$C_1$-$C_6$ alkyl groups may include any applicable chemical moieties. Examples of groups that may be substituted onto any of the above listed —$C_1$-$C_6$ alkyl groups include but are not limited to the following examples: halo, —$C_1$-$C_6$ alkyl, —O—($C_1$-$C_6$ alkyl), —OH, —CN, —COOR', —OC(O)R', —NHR', N(R')$_2$, —NHC(O)R' or —C(O)NHR' groups. The groups denoted R' above may be —H or any —$C_1$-$C_6$ alkyl.

An aryl group includes any unsubstituted or substituted phenyl or napthyl group. Examples of groups that may be substituted onto ay aryl group include, but are not limited to: halo, —$C_1$-$C_6$ alkyl, —O—($C_1$-$C_6$ alkyl), —OH, —CN, —COOR', —OC(O)R', NHR', N(R')2, —NHC(O), R', or —C(O)NEtR'. The group denoted R' may be —H or any —$C_1$-$C_6$ alkyl.

A $C_3$-$C_7$ cycloalkyl group includes any 3-, 4-, 5-, 6-, or 7-membered substituted or unsubstituted non-aromatic carbocyclic ring. Examples of $C_3$-$C_7$ cycloalkyl groups include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl, -1,4-cyclohexadienyl, -1,3-cycloheptadienyl, and-1,3,5-cycloheptatrienyl groups. Examples of groups that may be substituted onto $C_3$-$C_7$ cycloalkyl groups include, but are not limited to: -halo, —$C_1$-$C_6$ alkyl, —O—($C_1$-$C_6$ alkyl), —OH, —CN, —COOR', —OC(O)R', NHR', N(R')2, —NHC(O)R' or —C(O)NHR' groups. The groups denoted R' above include an —H or any unsubstituted —$C_1$-$C_6$ alkyl, examples of which are listed above. Halo groups include any halogen. Examples include but are not limited to —F, —Cl, —Br, or —I.

A heterocycle may be any optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, suitable substituents include halogen, halogenated C1-6 alkyl, halogenated C1-6 alkoxy, amino, amidino, amido, azido, cyano, guanidino, hydroxyl, nitro, nitroso, urea, OS(O)$_2$R; OS(O)$_2$OR, S(O)$_2$OR S(O)$_{0-2}$R, C(O)OR wherein R may be H, $C_1$-$C_6$ alkyl, aryl or 3 to 10 membered heterocycle) OP(O)OR$_1$OR$_2$, P(O)OR$_1$OR$_2$, SO$_2$NR$_1$R$_2$, NR$_1$SO$_2$R$_2$ C(R$_1$)NR$_2$ C(R$_1$)NOR$_2$, R1 and R2 may be independently H, $C_1$-$C_6$ alkyl, aryl or 3 to 10 membered heterocycle), NR$_1$C(O)R$_2$, NR$_1$C(O)OR$_2$, NR$_3$C(O)NR$_2$R$_1$, C(O)NR$_1$R$_2$, OC(O)NR$_1$R$_2$. For these groups, R$_1$, R$_2$ and R$_3$ are each independently selected from H, $C_1$-$C_6$ alkyl, aryl or 3 to 10 membered heterocycle or R$_1$ and R$_2$ are taken together with the atoms to which they are attached to form a 3 to 10 membered heterocycle.

Possible substituents of heterocycle groups include halogen (Br, Cl, I or F), cyano, nitro, oxo, amino, $C_{1-4}$ alkyl (e.g., $CH_3$, $C_2H_5$, isopropyl) $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxctanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienupyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

The disclosed compound and its intermediates may exist in different tautomeric forms. Tautomers include any structural isomers of different energies that have a low energy barrier to interconversion. One example is proton tautomers (prototropic tautomers.) In this example, the interconversions occur via the migration of a proton. Examples of prototropic tautomers include, but are not limited to keto-enol and imine-enamine isomerizations. In another example illustrated graphically below, proton migration between the 1-position and 3-position nitrogen atoms of the benzimidazole ring may occur. As a result, Formulas Ia and Ib are tautomeric forms of each other:

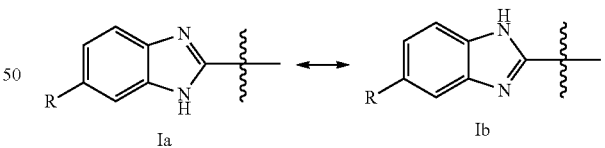

Ia    Ib

The invention further encompasses any other physiochemical or sterochemical form that the disclosed compound may assume. Such forms include diastereomers, racemates, isolated enantiomers, hydrated forms, solvated forms, or any other known or yet to be disclosed crystalline, polymorphic crystalline, or amorphous form. Amorphous forms lack a distinguishable crystal lattice and therefore lack an orderly arrangement of structural units. Many pharmaceutical compounds have amorphous forms. Methods of generating such chemical forms will be well known by one with skill in the art.

In some aspects of the invention the disclosed compound is in the form of a pharmaceutically acceptable salt. Pharmaceutically acceptable salts include any salt derived from an organic or inorganic acid. Examples of such salts include but are not limited to the following: salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl) benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated by one skilled in the art that such pharmaceutically acceptable salts may be used in the formulation of a pharmacological composition. Such salts may be prepared by reacting the disclosed compound with a suitable acid in a manner known by those skilled in the art.

The invention further encompasses aspects in which a protecting group is added to the compound. One skilled in the art would recognize that during the synthesis of complex molecules, one group on the disclosed compound may happen to interfere with an intended reaction that includes a second group on the compound. Temporarily masking or protecting the first group encourages the desired reaction. Protection involves introducing a protecting group to a group to be protected, carrying out the desired reaction, and removing the protecting group Removal of the protecting group may be referred to as deprotection. Examples of compounds to be protected in some syntheses include hydroxy groups, amine groups, carbonyl groups, carboxyl groups and thiols.

Many protective groups and reagents capable of introducing them into synthetic processes have been and are continuing to be developed today. A protecting group may result from any chemical synthesis that selectively attaches a group that is resistant to certain reagents to the chemical group to be protected without significant effects on any other chemical groups in the molecule, remains stable throughout the synthesis, and may be removed through conditions that do not adversely react with the protected group, nor any other chemical group in the molecule. Multiple protecting groups may be added throughout a synthesis and one skilled in the art would be able to develop a strategy for specific addition and removal of the protecting groups to and from the groups to be protected.

Protecting groups, reagents that add those groups, preparations of those reagents, protection and deprotection strategies under a variety of conditions, including complex syntheses with mutually complementary protecting groups are all well known in the art. Nonlimiting examples of all of these may be found in Green et al, *Protective Groups in Organic Chemistry* $2^{nd}$ Ed., (Wiley 1991), and Harrison et al, *Compendium of Synthetic Organic Methods*, Vols. 1-8 (Wiley, 1971-1996) both of which hereby incorporated by reference in its entirety.

Racemates, individual enantiomers, or diasteromers of the disclosed compound may be prepared by specific synthesis or resolution through any method now known or yet to be disclosed. For example, the disclosed compound may be resolved into it enantiomers by the formation of diasteromeric pairs through salt formation using an optically active acid. Enantiomers are fractionally crystallized and the free base regenerated. In another example, enantiomers may be separated by chromatography. Such chromatography may be any appropriate method now known or yet to be disclosed that is appropriate to separate enantiomers such as HPLC on a chiral column.

The invention further encompasses pharmaceutical compositions that include the disclosed compound as an ingredient. Such pharmaceutical compositions may take any physical form necessary depending on a number of factors including the desired method of administration and the physicochemical and stereochemical form taken by the disclosed compound or pharmaceutically acceptable salts of the compound. Such physical forms include a solid, liquid, gas, sol, gel, aerosol, or any other physical form now known or yet to be disclosed. The concept of a pharmaceutical composition including the disclosed compound also encompasses the disclosed compound or a pharmaceutically acceptable salt thereof without any other additive. The physical form of the invention may affect the route of administration and one skilled in the art would know to choose a route of administration that takes into consideration both the physical form of the compound and the disorder to be treated. Pharmaceutical compositions that include the disclosed compound may be prepared using methodology well known in the pharmaceutical art. A pharmaceutical composition that includes the disclosed compound may include a second effective compound of a distinct chemical formula from the disclosed compound. This second effective compound may have the same or a similar molecular target as the target or it may act upstream or downstream of the molecular target of the disclosed compound with regard to one or more biochemical pathways.

Pharmaceutical compositions including the disclosed compound include materials capable of modifying the physical form of a dosage unit. In one nonlimiting example, the composition includes a material that forms a coating that holds in the compound. Materials that may be used in such a coating, include, for example, sugar, shellac, gelatin, or any other inert coating agent.

Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or tri-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in a majority of patients.

Pharmaceutical compositions that include the disclosed compound may also include a pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, oils (including petroleum, animal, vegetable or synthetic oils.) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including the disclosed compound may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions including the disclosed compound may be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

Cancer cells include any cells derived from a tumor, neoplasm, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Expansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include caspase dependent and independent pathways, autophagy, necrosis, apoptosis, and mitochondrial dependent and independent processes and further include any such processes yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macophages and CD8+ T cells) or endothelial cells that may differentiate into blood vessel structures in the process of angiogenesis or vasculogenesis.

Determination of an effective amount of the disclosed compound is within the capability of those skilled in the art, especially in light of the detailed disclosure provided herein. The effective amount of a pharmaceutical composition used to effect a particular purpose as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals.

The toxicity and therapeutic efficacy of a pharmaceutical composition may be determined by standard pharmaceutical procedures in cell cultures or animals. Examples include the determination of the $IC_{50}$ (the half maximal inhibitory concentration) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of the disclosed compound to results in the slowing of expansion of the cancer cells would preferably result in a concentration at or near the target tissue that is effective in slowing cellular exapansion in neoplastic cells, but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of the disclosed compound encompasses any method of dosing of a compound. Dosing of the disclosed compound may include single or multiple administrations of any of a number of pharmaceutical compositions that include the disclosed compound as an active ingredient. Examples include a single administration of of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the disclosed compound may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of the compound. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions including the disclosed compound may be used in methods of treating cancer. Such methods involve the administration of a therapeutic amount of a pharmaceutical composition that includes the disclosed compound and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-79). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype). Further examples include leukoplakia, in which a benign-appearing hyperplastic or dysplastic lesion of the epithelium, or Bowen's disease, a carcinoma in situ, are pre-neoplastic lesions indicative of the desirability of prophylactic intervention. In another example, fibrocystic disease including cystic hyperplasia, mammary dysplasia, adenosis, or benign epithelial hyperplasia is indicates desirability of prophylactic intervention.

In some aspects of the invention, use of the disclosed compound may be determined by one or more physical factors such as tumor size and grade or one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, Arch. Pathol. Lab. Med. 124:966-78, 2000. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a trans-membrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t (14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition including the disclosed compound and another treatment modality. Such treatment modalities include but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition including the disclosed compound is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, other CNS neoplasms, or any other such tumor now known or yet to be disclosed.

Examples of pharmaceutical compositions that may be used in combination with the disclosed compound may include nucleic acid binding compositions such as cis-diamminedichloro platinum (II) (cisplatin), doxorubicin, 5-fluorouracil, taxol, and topoisomerase inhibitors such as etoposide, teniposide, irinotecan and topotecan. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of phannaceutical compositions that may be used in combination with the pharmaceutical composition including the disclosed compound are hematopoietic colony stimulating factors. Examples of hematopoietic colony stimulating factors include, but are not limited to, filgrastim, sargramostim, molgramostim and epoietin alfa. Alternatively, the pharmaceutical composition including the disclosed compound may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include the disclosed compound may include analgesic agents. Such agents may be opioid or non-opioid analgesic. Non-limiting examples of opioid analgesics include morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

In other aspects of the invention, pharmaceutical compositions including the disclosed compound may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including the disclosed compound may then be administered to the patient prior to restoring the entity's bone marrow by addition of either the patient's own or donor stem cells.

Cancers that may be treated by pharmaceutical compositions including the disclosed compound either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms'tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may be treated by pharmaceutical compositions including the disclosed compound include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polyeythemia vera.

Examples that represent different aspects of the invention follow. Such examples should not be construed as limiting the scope of the disclosure. Alternative mechanistic pathways and analogous structures within the scope of the invention would be apparent to those skilled in the art.

EXAMPLES

Elements and acts in the example are intended to illustrate the invention for the sake of simplicity and have not necessarily been rendered according to any particular sequence or embodiment. The example is also intended to establish possession of the invention by the Inventors.

N-(2-aminophenyl)-4-(1-isopropyl-1H-benzo[d]imidazol-2-ylamino)benzamide. ID #1

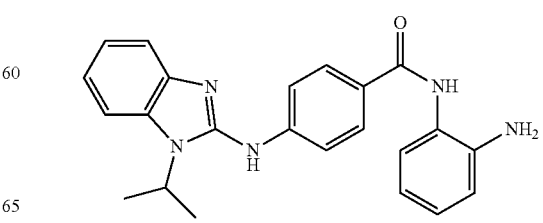

15

N-hydroxy-4-(1-methyl-1H-benzo[d]imidazol-2-ylamino)benzamide. ID #2

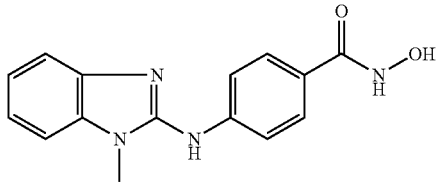 [SMILES: Cn1c(Nc2ccc(C(=O)NO)cc2)nc2ccccc21]

4-(1-cyclobutyl-1H-benzo[d]imidazol-2-ylamino)-N-hydroxybenzamide. ID #3

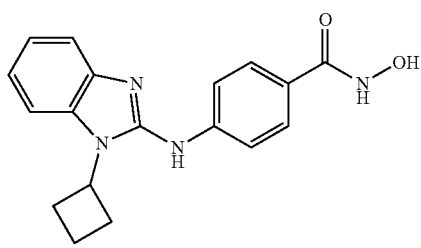 [SMILES: O=C(NO)c1ccc(Nc2nc3ccccc3n2C2CCC2)cc1]

N-hydroxy-4-(1-(2-methoxyethyl)-1H-benzo[d]imidazol-2-ylamino)benzamide. ID #4

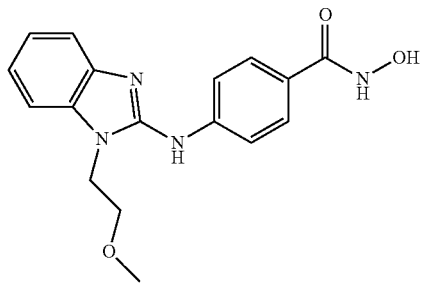 [SMILES: COCCn1c(Nc2ccc(C(=O)NO)cc2)nc2ccccc21]

4-(1-cyclopentyl-1H-benzo[d]imidazol-2-ylamino)-N-hydroxybenzamide. ID #5

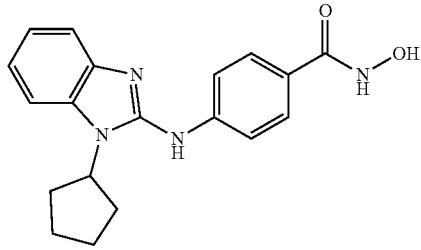 [SMILES: O=C(NO)c1ccc(Nc2nc3ccccc3n2C2CCCC2)cc1]

16

4-(5-bromo-1-isopropyl-1H-benzo[d]imidazol-2-ylamino)-N-hydroxybenzamide. ID #6

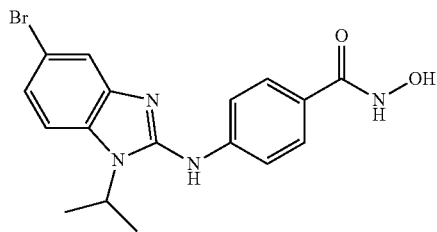 [SMILES: CC(C)n1c(Nc2ccc(C(=O)NO)cc2)nc2cc(Br)ccc21]

4-(6-bromo-1-isopropyl-1H-benzo[d]imidazol-2-ylamino)-N-hydroxybenzamide. ID #7

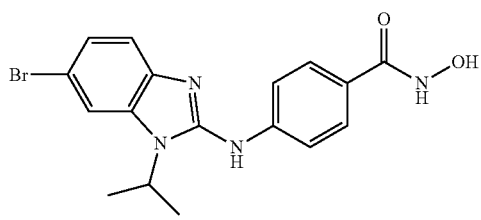 [SMILES: CC(C)n1c(Nc2ccc(C(=O)NO)cc2)nc2ccc(Br)cc21]

N-hydroxy-4-(1-(2-methoxyethyl)-5-phenyl-1H-benzo[d]imidazol-2-ylamino)benzamide. ID #8

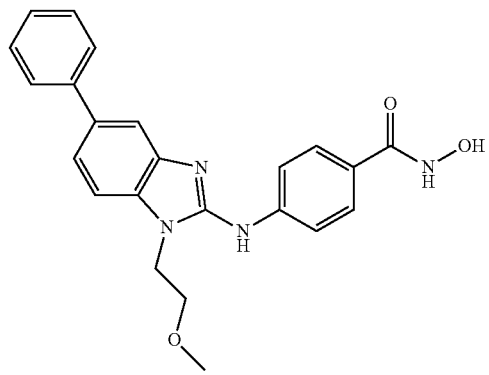 [SMILES: COCCn1c(Nc2ccc(C(=O)NO)cc2)nc2cc(-c3ccccc3)ccc21]

N-hydroxy-4-(1-(3-methoxypropyl)-1H-benzo[d]imidazol-2-ylamino)benzamide. ID #9

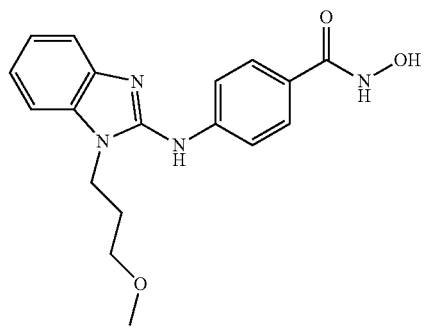 [SMILES: COCCCn1c(Nc2ccc(C(=O)NO)cc2)nc2ccccc21]

4-(5-bromo-1-(2-methoxyethyl)-1H-benzo[d]imidazol-2-ylamino)-N-hydroxybenzamide. ID #10

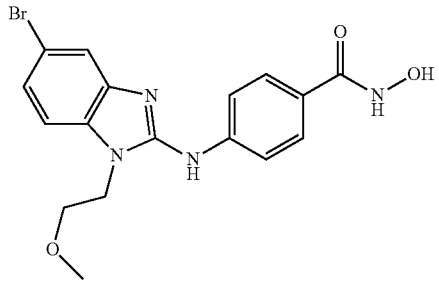 [SMILES: COCCn1c(Nc2ccc(C(=O)NO)cc2)nc2cc(Br)ccc21]

N-hydroxy-4-(1-(2-hydroxyethyl)-1H-benzo[d]imidazol-2-ylamino)benzamide. ID #11

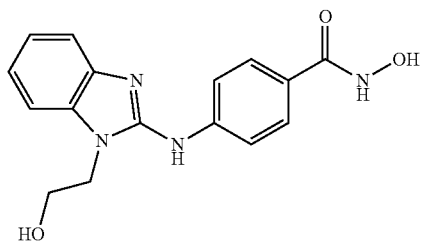 [SMILES: O=C(NO)c1ccc(Nc2nc3ccccc3n2CCO)cc1]

4-(5-fluoro-1-(2-methoxyethyl)-1H-benzo[d]imidazol-2-ylamino)-N-hydroxybenzamide. ID #12

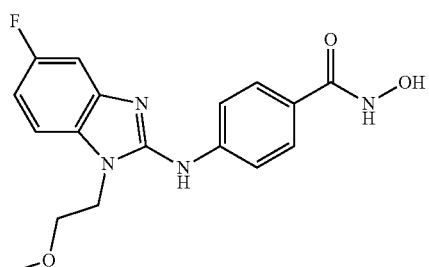

N-hydroxy-4-(1-(2-isopropoxyethyl)-1H-benzo[d]imidazol-2-ylamino)benzamide. ID #13

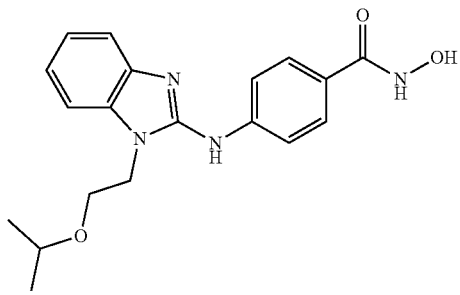 [SMILES: CC(C)OCCn1c(Nc2ccc(C(=O)NO)cc2)nc2ccccc21]

4-(5-(3-fluorophenyl)-1-(2-methoxyethyl)-1H-benzo[d]imidazol-2-ylamino)-N-hydroxybenzamide. ID #14

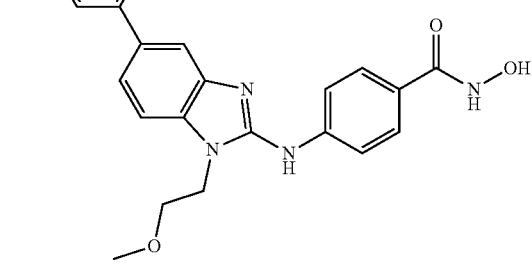

N-hydroxy-4-(1-(2-methoxyethyl)-5-(pyrimidin-5-yl)-1H-benzo[d]imidazol-2-ylamino)benzamide. ID #15

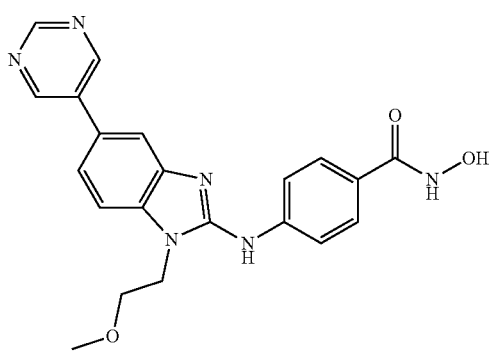 [SMILES: COCCn1c(Nc2ccc(C(=O)NO)cc2)nc2cc(-c3cncnc3)ccc21]

4-(5-cyclopropyl-1-(2-methoxyethyl)-1H-benzo[d]imidazol-2-ylamino)-N-hydroxybenzamide. ID #16

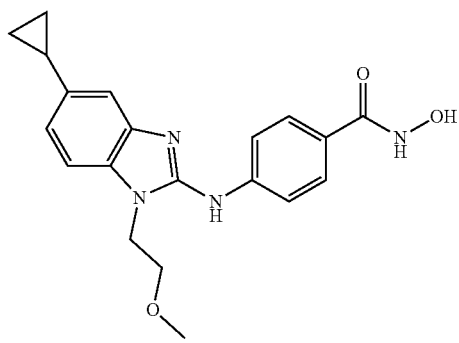 [SMILES: COCCn1c(Nc2ccc(C(=O)NO)cc2)nc2cc(C3CC3)ccc21]

4-(5-bromo-1-(2-(dimethylamino)ethyl)-1H-benzo[d]imidazol-2-ylamino)-N-hydroxybenzamide. ID #17

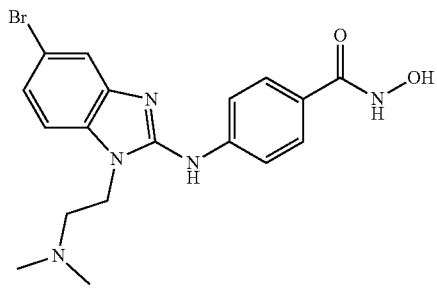 [SMILES: CN(C)CCn1c(Nc2ccc(C(=O)NO)cc2)nc2cc(Br)ccc21]

N-hydroxy-4-(1-isopropyl-5-(pyrimidin-5-yl)-1H-benzo[d]imidazol-2-ylamino)benzamide. ID #18

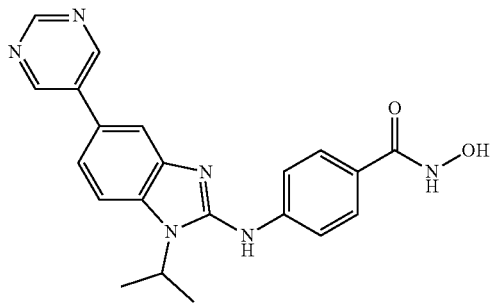 [SMILES: CC(C)n1c(Nc2ccc(C(=O)NO)cc2)nc2cc(-c3cncnc3)ccc21]

N-hydroxy-4-(1-isopropyl-5-(pyridin-3-yl)-1H-benzo[d]imidazol-2-ylamino)benzamide. ID #19

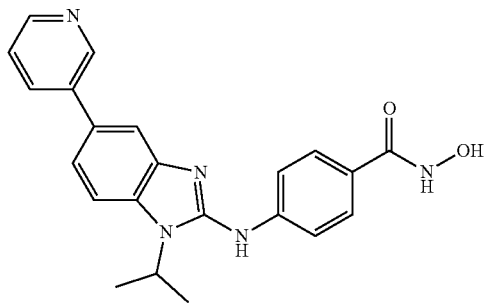 [SMILES: CC(C)n1c(Nc2ccc(C(=O)NO)cc2)nc2cc(-c3cccnc3)ccc21]

N-(2-aminophenyl)-4-(1-(2-methoxyethyl)-1H-benzo[d]imidazol-2-ylamino)benzamide. ID #20

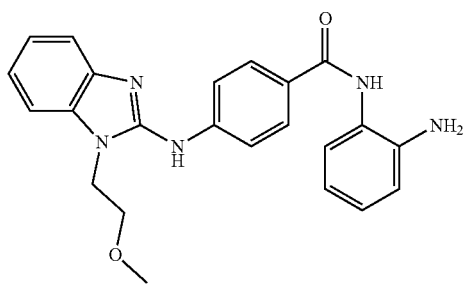 [SMILES: COCCn1c(Nc2ccc(C(=O)Nc3ccccc3N)cc2)nc2ccccc21]

4-(6-fluoro-1-(2-methoxyethyl)-1H-benzo[d]imidazol-2-ylamino)-N-hydroxybenzamide. ID #21

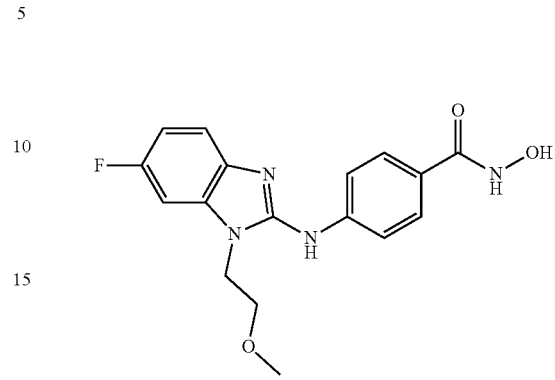

4-(4-fluoro-1-(2-methoxyethyl)-1H-benzo[d]imidazol-2-ylamino)-N-hydroxybenzamide. ID #22

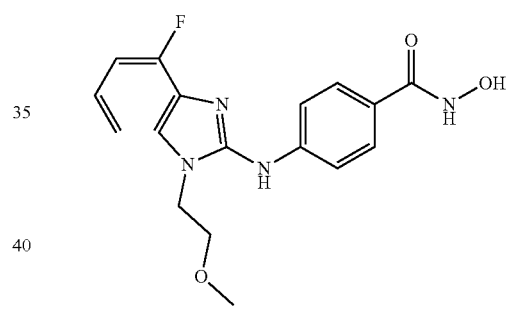

N-hydroxy-4-(1-isopropyl-5-(methoxymethyl)-1H-benzo[d]imidazol-2-ylamino)benzamide. ID #23

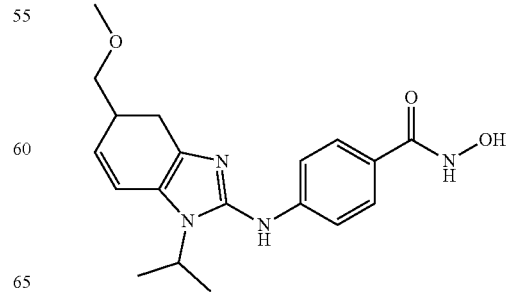

Scheme 1
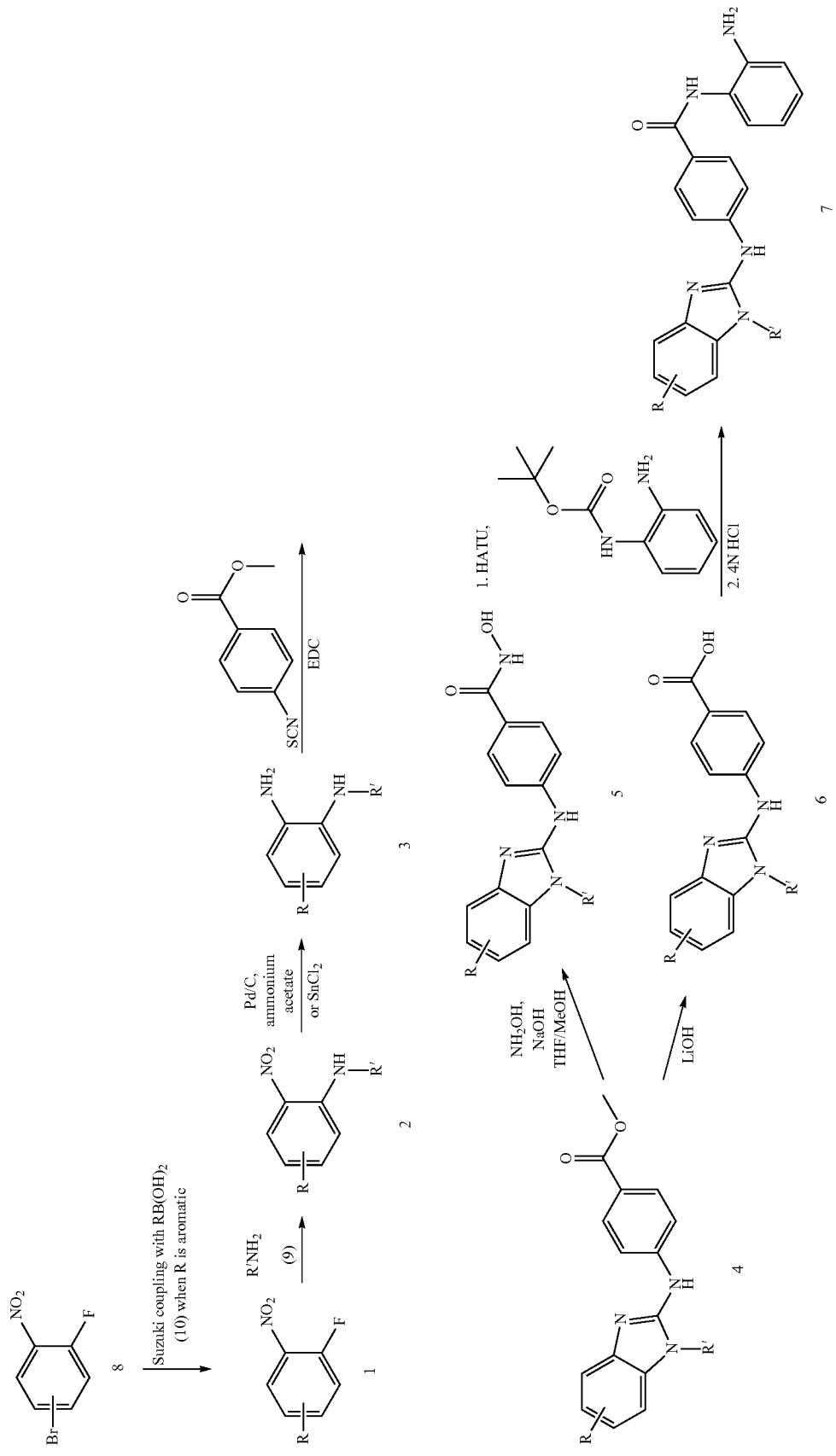

The synthesis of the compounds begins with a 2-fluoronitrobenzene of formula 1 (Scheme 1). When R is an aromatic ring, the 2-fluoronitrobenzene of formula 1 can be prepared from the corresponding bromide of formula 8 through a Suzuki cross coupling reaction. An amine addition with R'NH2 9 generates a nitrobenzene of formula 2, which is reduced to form a dianiline of formula 3. N-(3-Dimethylaminopropyl)-N-ethylcarbodiimide (EDC) mediated cyclization of a dianiline of formula 3 with methyl 4-isothiocyanatobenzoate affords a methyl ester of formula 4. Treatment of a methyl ester of formula 4 with hydroxylamine and sodium hydroxide solution results in the formation of a hydroxamic acid of formula 5. Alternatively, hydrolysis of a methyl ester of formula 4 provides a carboxylic acid of formula 6. Subsequent amide formation reaction with tert-butyl 2-aminophenylcarbamate followed by removal of the protective group generates an amide of formula 7.

In certain aspects, the amine addition with R'NH2 9 utilizes a cycloalkylmethylamine. For example in the amine addition with R'NH2 9, compound 9 is cyclopropylmethylamine, cyclobutylmethylamine, cyclopentylmethylamine, cyclohexylmethylamine, or cycloheptylmethylamine.

Example 1

Synthesis of N-(2-aminophenyl)-4-(1-isopropyl-1H-benzo[d]imidazol-2-ylamino)benzamide. (Compound 1D #1)

Isopropyl amine (3 mL) is added to a solution of 1-fluoro-2-nitrobenzene (500 mg, 3.55 mmol) in ethanol. The reaction may be stirred at room temperature overnight and concentrated. The residue may be purified, for example by Biotage column chromatography to give N-isopropyl-2-nitroaniline (590 mg).

Ammonium formate (960 mg, 15.0 mmol) is added to a solution of N-isopropyl-2-nitroaniline (550 mg, 3.03 mmol) in methanol. This may be followed by a catalytic amount of palladium on carbon (5%). The mixture may be refluxed overnight, cooled to room temperature and filtered. The filtrate may be concentrated by any applicable and the residue may be purified, for example by Biotage column chromatography to give N1-isopropylbenzene-1,2-diamine (398 mg)

N-(3-Dimethylaminopropyl)-N'-ethylcarbodiimide (EDC, 206 mg, 1.34 mmol) is added to a solution of N1-isopropylbenzene-1,2-diamine (100 mg, 0.67 mmol) and methyl 4-isothiocyanatobenzoate (138 mg, 0.67 mmol) in tetrahydrofuran. The reaction may be heated to reflux for a time period (for example 2 hours) and cooled to room temperature. The mixture may be diluted with ethyl acetate, filtered and concentrated. The residue may be purified by any method, including Biotage column chromatography to give methyl 4-(1-isopropyl-1H-benzo[d]imidazol-2-ylamino)benzoate (122 mg)

1 N lithium hydroxide solution (1.2 mL, 1.2 mmol) is added to a solution of methyl 4-(1-isopropyl-1H-benzo[d]imidazol-2-ylamino)benzoate (122 mg, 0.395 mmol). The reaction may be stirred at room temperature overnight and concentrated. 1 N hydrochloride solution may be added to the residue and a white precipitate collected by filtration to give 4-(1-isopropyl-1H-benzo[d]imidazol-2-ylamino)benzoic acid (66 mg)

2-(7-Aza-1H-benzotriazole-1-yl)-1,1,3,3-tetramethyluronium hexafluorophosphate (HATU, 62 mg, 0.16 mmol) was added to a solution of 4-(1-isopropyl-1H-benzo[d]imidazol-2-ylamino)benzoic acid (40 mg, 0.13 mmol), tert-butyl 2-aminophenylcarbamate (34 mg, 0.16 mmol) and N,N-diisopropylethylamine (0.047 mL, 0.27 mmol. The reaction may be stirred at room temperature for an appropriate time period such as 2 hrs and quenched by water. The mixture may be extracted with any appropriate agent, such as ethyl acetate, and concentrated. The residue may be purified by any appropriate method, including Biotage column chromatography to give tert-butyl 2-(4-(1-isopropyl-1H-benzo[d]imidazol-2-ylamino)benzamido)phenylcarbamate (58 mg)

Tert-butyl 2-(4-(1-isopropyl-1H-benzo[d]imidazol-2-ylamino)benzamido)phenylcarbamate (58 mg) is treated with 2 mL of 4 N hydrogen chloride in dioxane. The reaction may be stirred at room temperature for 1 hr and concentrated. The residue may be purified by any appropriate method, including Biotage column chromatography to give compound #1(19 mg). MS (calculated for M+1: 386; found 386).

Example 2

Synthesis of N-hydroxy-4-(1-(2-methoxyethyl)-1H-benzo[d]imidazol-2-ylamino)benzamide (Compound ID #4)

2-methoxyethaneamine (3 mL) is added to a solution of 1-fluoro-2-nitrobenzene (400 mg, 2.84 mmol) in ethanol. The reaction may be stirred at room temperature for an appropriate time period (such as overnight) and concentrated. The residue may be purified by any appropriate method including Biotage column chromatography to give N-(2-methoxyethyl)-2-nitroaniline (477 mg).

Ammonium formate (727 mg, 11.3 mmol) followed by a catalytic amount of palladium on carbon (5%) is added to a solution of N-(2-methoxyethyl)-2-nitroaniline (426 mg, 2.17 mmol) in methanol. The mixture may be refluxed for an appropriate time period (such as overnight), cooled to an appropriate temperature (such as room temperature) and filtered. The filtrate may be concentrated and the residue may purified by Biotage column chromatography to give N1-(2-methoxyethyl)benzene-1,2-diamine (319 mg)

N-(3-Dimethylaminopropyl)-N'-ethylcarbodiimide (EDC, 791 mg) is added to a solution of N1-(2-methoxyethyl)benzene-1,2-diamine (311 mg, 1.87 mmol) and methyl 4-isothiocyanatobenzoate (328 mg, 1.70 mmol) in tetrahydrofuran. The reaction may be heated to reflux for 2 hr and cooled to room temperature. The mixture may be diluted in an appropriate solvent such as ethyl acetate, filtered and concentrated. The residue may be purified by any appropriate method, including Biotage column chromatography to give methyl 4-(1-(2-methoxyethyl)-1H-benzo[d]imidazol-2-ylamino)benzoate (381 mg).

3 mL of hydroxylamine (50% in water) followed by sodium hydroxide solution (1 N, 1.2 mL) is added to a solution of 4-(1-(2-methoxyethyl)-1H-benzo[d]imidazol-2-ylamino)benzoate (160 mg, 0.64 mmol) in a mixture of tetrahydrofuran/methanol (4:1). The mixture may be stirred at room temperature overnight and concentrated. The residue may be acidified with an appropriate acid such as 1 N HCl and purified by an appropriate purification method such as Biotage column chromatography to give compound #4 (115 mg). $^1$HNMR (CD3OD): 7.74 (d, 2H), 7.66 (d, 2H), 7.42 (dd, 1H), 7.32 (dd, 1H), 7.13 (dd, 2H), 4.37 (t, 2H), 3.75 (t, 2H), 3.37 (s, 3H). MS (calculated for M+1: 327; found 327).

Example 3

Synthesis of 4-(5-bromo-1-isopropyl-1H-benzo[d]imidazol-2-ylamino)-N-hydroxybenzamide (Compound ID #6)

Isopropylamine (3 mL) is added to a solution of 4-bromo-1-fluoro-2-nitrobenzene (700 mg, 3.18 mmol) in ethanol. The reaction may be stirred for an appropriate time at an appropriate temperature, such as room temperature for overnight and concentrated. The residue may be purified by any appropriate method such as Biotage column chromatography to give 4-bromo-N-isopropyl-2-nitroaniline (770 mg).

Tin(II) chloride (1.69 g, 8.90 mmol) is added to a solution of 4-bromo-N-isopropyl-2-nitroaniline (770 mg, 2.97 mmol) in ethanol. The mixture may be heated to reflux for an appropriate time (such as 4 hr) and cooled. 4 N sodium hydroxide is added to the solution which then may be filtered. The filtrate is extracted with ethyl acetate. The combined organic layer may be washed with brine and concentrated. The residue may be purified by any appropriate method including Biotage column chromatography to give 4-bromo-N1-isopropylbenzene-1,2-diamine (513 mg).

N-(3-Dimethylaminopropyl)-N'-ethylcarbodiimide (EDC, 331 mg, 2.18 mmol) is added to a solution of 4-bromo-N1-isopropylbenzene-1,2-diamine (180 mg, 0.786 mmol) and methyl 4-isothiocyanatobenzoate (140 mg, 0.725 mmol) in tetrahydrofuran was added. The reaction was heated to reflux for 2 hr and cooled to room temperature. The mixture was diluted with ethyl acetate and washed with 1 N HCl and saturated sodium bicarbonate solution. The organic layer was concentrated and purified by Biotage column chromatography to give methyl 4-(5-bromo-1-isopropyl-1H-benzo[d]imidazol-2-ylamino)benzoate (202 mg)

2.3 mL of hydroxylamine (50% in water) followed by sodium hydroxide solution (1 N, 0.8 mL) is added to a solution of methyl 4-(5-bromo-1-isopropyl-1H-benzo[d]imidazol-2-ylamino)benzoate (100 mg, 0.258 mmol) in a mixture of tetrahydrofuran/methanol (4:1). The mixture was stirred at room temperature overnight and concentrated. The residue may be acidified by any appropriate acid such as 1N HCl and purified by any appropriate method such as Biotage column chromatography to afford compound #6 (56 mg). MS (calculated for M+1: 390; found 390).

Example 4

Synthesis of N-hydroxy-4-(1-(2-methoxyethyl)-5-phenyl-1H-benzo[d]imidazol-2-ylamino)benzamide. (Compound ID #8)

Dioxane is added under a nitrogen atmosphere to a mixture of 4-bromo-1-fluoro-2-nitrobenzene (220 mg, 1.00 mmol), benzeneboronic acid (143 mg, 1.20 mmol), potassium phosphate (636 mg, 3.00 mmol) and Tetrakis(triphenylphosphine)-palladium(0) (55 mg, 0.05 mmol). The reaction may be heated to an appropriate temperature such as 90° C., stirred for an appropriate time, such as overnight, and filtered. The filtrate may be concentrated and purified by Biotage column chromatography to give 4-fluoro-3-nitrobiphenyl (200 mg).

2-methoxyethaneamine (1.5 mL) is added to a solution of 4-fluoro-3-nitrobiphenyl (200 mg, 0.92 mmol) in ethanol. The reaction may be stirred at room temperature overnight and concentrated. The residue may be purified by any appropriate method, such as Biotage column chromatography to give N-(2-methoxyethyl)-3-nitrobiphenyl-4-amine (228 mg).

Ammonium formate (360 mg, 5.6 mmol), followed by a catalytic amount of palladium on carbon (5%) was added to a solution of N-(2-methoxyethyl)-3-nitrobiphenyl-4-amine (228 mg, 0.84 mmol) in methanol. The mixture may be refluxed overnight, cooled to an appropriate temperature, and filtered. The filtrate may be concentrated and the residue may be purified by any appropriate method, including Biotage column chromatography to give N-(2-methoxyethyl)-3-nitrobiphenyl-4-amine (182 mg).

N-(3-Dimethylaminopropyl)-N'-ethylcarbodiimide (EDC, 200 mg, 1.44 mg) is added to a solution of N-(2-methoxyethyl)-3-nitrobiphenyl-4-amine (119 mg, 0.48 mmol) and methyl 4-isothiocyanatobenzoate (83 mg, 0.43 mmol) in tetrahydrofuran. The reaction may reflux for an appropriate time period, such as 2 hours and cooled. The mixture may be diluted with ethyl acetate, filtered and concentrated. The residue may be purified by any appropriate method including Biotage column chromatography to give methyl 4-(1-(2-methoxyethyl)-5-phenyl-1H-benzo[d]imidazol-2-ylamino)benzoate (96 mg)

1.8 mL of hydroxylamine (50% in water) followed by sodium hydroxide solution (1 N, 0.36 mL) is added to a solution of methyl 4-(1-(2-methoxyethyl)-5-phenyl-1H-benzo[d]imidazol-2-ylamino)benzoate (74 mg, 0.18 mmol) in a mixture of tetrahydrofuran/methanol (4:1). The mixture may be stirred at room temperature overnight and concentrated. The residue may be acidified with any appropriate acid such as 1 N HCl and purified by any appropriate method including Biotage column chromatography to afford compound #8 (36 mg). MS (calculated for M+1: 403; found 403).

Example 5

N-hydroxy-4-(1-methyl-1H-benzo[d]imidazol-2-ylamino)benzamide. (Compound ID #2)

The compound was prepared using methylamine and otherwise by following the synthesis method of Example 2. MS (calculated for M+1: 283; found 283).

Example 6

4-(1-cyclobutyl-1H-benzo[d]imidazol-2-ylamino)-N-hydroxybenzamide. (Compounds 1D #3)

The compound was prepared using cyclobutylamine and otherwise by following the synthesis method of Example 2. MS (calculated for M+1: 323; found 323).

Example 7

4-(1-cyclopentyl-1H-benzo[d]imidazol-2-ylamino)-N-hydroxybenzamide. (Compound ID #5)

The compound was prepared using cyclopentylamine and otherwise by following the synthesis method of Example 2. MS (calculated for M+1: 337; found 337).

Example 8

4-(6-bromo-1-isopropyl-1H-benzo[d]imidazol-2-ylamino)-N-hydroxybenzamide. (Compound ID #7)

The compound was prepared using 4-bromo-2-fluoro-1-nitrobenzene and otherwise by following the synthesis method of Example 4. MS (calculated for M+1: 390; found 390).

Example 9

N-hydroxy-4-(1-(3-methoxypropyl)-1H-benzo[d]imidazol-2-ylamino)benzamide. (Compound ID #9)

The compound was prepared using 3-methoxypropan-1-amine and otherwise by following the synthesis method of Example 2. MS (calculated for M+1: 341; found 341).

Example 10

4-(5-bromo-1-(2-methoxyethyl)-1H-benzo[d]imidazol-2-ylamino)-N-hydroxybenzamide. (Compound ID #10)

The compound was prepared using 2-methoxyethanamine and otherwise by following the synthesis method of Example 3. MS (calculated for M+1: 406; found 406).

Example 11

N-hydroxy-4-(1-(2-hydroxyethyl)-1H-benzo[d]imidazol-2-ylamino)benzamide. (Compound ID #11)

The compound was prepared using 2-aminoethanol and otherwise by following the synthesis method of Example 2. MS (calculated for M+1: 313; found 313).

Example 12

4-(5-fluoro-1-(2-methoxyethyl)-1H-benzo[d]imidazol-2-ylamino)-N-hydroxybenzamide. (Compound 1D #12)

The compound was prepared using 1,4-difluoro-2-nitrobenzene and otherwise by following the synthesis method of Example 2. MS (calculated for M+1: 345; found 345).

Example 13

N-hydroxy-4-(1-(2-isopropoxyethyl)-1H-benzo[d]imidazol-2-ylamino)benzamide. (Compound ID #13)

The compound was prepared using 2-isopropoxyethanamine and otherwise by following the synthesis method of Example 2. MS (calculated for M+1: 355; found 355).

Example 14

4-(5-(3-fluorophenyl)-1-(2-methoxyethyl)-1H-benzo[d]imidazol-2-ylamino)-N-hydroxybenzamide. (Compound ID #14)

The compound was prepared using 1,5-difluoro-2-nitrobenzene and otherwise by following the synthesis method of Example 2. MS (calculated for M+1: 345; found 345).

Example 15

N-hydroxy-4-(1-(2-methoxyethyl)-5-(pyrimidin-5-yl)-1H-benzo[d]imidazol-2-ylamino)benzamide. (Compound ID #15)

The compound was prepared using 5-pyrimidineboronic acid and 2-methoxyethanamine and otherwise by following the synthesis method of Example 4. MS (calculated for M+1: 405; found 405).

Example 16

4-(5-cyclopropyl-1-(2-methoxyethyl)-1H-benzo[d]imidazol-2-ylamino)-N-hydroxybenzamide. (Compound ID #16)

The compound was prepared using cyclopropylboronic acid and 2-methoxyethanamine and otherwise by following the synthesis method of Example 4. MS (calculated for M+1: 367; found 367).

Example 17

4-(5-bromo-1-(2-(dimethylamino)ethyl)-1H-benzo[d]imidazol-2-ylamino)-N-hydroxybenzamide. (Compound ID #17)

The compound was prepared using N1,N1-dimethylethane-1,2-diamine and otherwise by following the synthesis method of Example 3. MS (calculated for M+1: 419; found 419).

Example 18

N-hydroxy-4-(1-isopropyl-5-(pyrimidin-5-yl)-1H-benzo[d]imidazol-2-ylamino)benzamide. (Compound 1D #18)

The compound was prepared using 3-pyrimidineboronic acid and otherwise by following the synthesis method of Example 4. MS (calculated for M+1: 389; found 389).

Example 19

N-hydroxy-4-(1-isopropyl-5-(pyridin-3-yl)-1H-benzo[d]imidazol-2-ylamino)benzamide. (Compound ID #19)

The compound was prepared using 3-pyridineboronic acid and otherwise by following the synthesis method of Example 4. MS (calculated for M+1: 388; found 388).

Example 20

N-(2-aminophenyl)-4-(1-(2-methoxyethyl)-1H-benzo[d]imidazol-2-ylamino)benzamide. (Compound ID #20)

The compound was prepared using 2-methoxyethanamine and otherwise by following the synthesis method of Example 1. MS (calculated for M+1: 402; found 402).

Example 21

4-(6-fluoro-1-(2-methoxyethyl)-1H-benzo[d]imidazol-2-ylamino)-N-hydroxybenzamide. (Compound ID #21)

The compound was prepared using 2,4-difluoro-1-nitrobenzene and otherwise by following the synthesis method of Example 2. MS (calculated for M+1: 345; found 345).

Example 22

4-(4-fluoro-1-(2-methoxyethyl)-1H-benzo[d]imidazol-2-ylamino)-N-hydroxybenzamide. (Compound ID #22)

The compound was prepared using 1,3-difluoro-2-nitrobenzene and otherwise by following the synthesis method of Example 2. MS (calculated for M+1: 345; found 345).

Example 23

N-hydroxy-4-(1-isopropyl-5-(methoxymethyl)-1H-benzo[d]imidazol-2-ylamino)benzamide. (Compound ID #23)

The compound was prepared using 1-fluoro-4-(methoxymethyl)-2-nitrobenzene and otherwise by following the synthesis method of Example 2. MS (calculated for M+1: 355; found 355).

Example 24

Cell viability in the presence of varying concentrations of the above listed compounds at different time points was used to assess cytotoxicity and the effect of the compounds on cell proliferation. $IC_{50}$ (or percent activity) data for the disclosed compounds in the SKOV3 and A2780 cell lines are summarized in Table 1.

Cell Viability Assay—

Cell viability was measured by the CellTiter-Blue® cell viability assay Promega (Madison, Wis.). This procedure measures the conversion of the indicator dye (resazurin) to resorufin, an indicator of cell viability. Following treatment, growth media was removed and cells were incubated with 20 μl of CellTiter-Blue® Reagent and growth media for 1-4 hours at 37° C. Fluorescence values were measured at 535/590 nm using a Beckman-Coulter DTX-880 microplate reader.

Single Agent Studies—

Cells were grown to 70% confluency, trypsinized, counted, and seeded in 96 well flat-bottom plates at a final concentration of $2.5 \times 10^3$-$5 \times 10^3$ cells/well (Day 0). Cells were allowed to incubate in growth media for 24 hours to allow for maximum adhesion. Treatment with the test agents or standard agents began on Day 1 and continued for 72 hours. At the 72 hour timepoint, treatment containing media was removed. Viable cell numbers are quantified by the CellTiter-Blue® cell viability assay as described above. Experiments were repeated at least twice with the same concentrations to determine growth inhibitory activity. Results from these studies were used to calculate an $IC_{50}$ value (concentration of drug that inhibits cell growth by 50 percent of control) for each compound.

Data Collection—

For single agent and combination studies, data from each experiment was collected and expressed as % Cell Growth using the following calculation:

% Cell Growth=$(f_{test}/f_{vehicle}) \times 100$

Where $f_{test}$ is the fluorescence of the tested sample, and $f_{vehicle}$ is the fluorescence of the vehicle in which the drug is dissolved. Dose response graphs and $IC_{50}$ values were generated using Prism 4 software (GraphPad) using the following equation:

$$Y = \frac{(\text{Top} - \text{Bottom})}{(1 + 10^{((logIC50-X)-HillSlope)})}$$

Where X is the logarithm of concentration and Y is the response. Y starts at the Bottom and goes to Top with a sigmoid shape.

Further, the in vivo efficacy studies of compound ID #4 in A2780 xenograft models is shown in FIG. 1. In vivo efficacy of the disclosed compound was tested through a human ovarian tumor xenograft model. Female Ncr nude mice were inoculated with $1 \times 10^7$ A2780 human ovarian cells suspended in a mixture of 50% Matrigel and 50% tissue culture media in a total volume of 100 μl. Four days following inoculation, the mice were pair-matched into four groups of 7-8 mice per group at an average tumor weight of 157 mg per group. Group 1 (G1) was treated with vehicle only daily for 14 days. Group 3 (G3) was treated with Compound ID #4 (T062) at 100 mg/kg daily for 14 days. Group 5 (G5) was treated with Doxil at 3 mg/kg on Day 1 only. Group 6 (G6) was treated with Compound ID #4 (T062) at 50 mg/kg (daily for 14 days) plus Doxil at 3 mg/kg on Day 1 only. Group 7 (G7) was treated with Compound ID #4 (T062) at 100 mg/kg (daily for 14 days) plus Doxil at 3 mg/kg on Day 1 only. Vehicle and Compound ID #4 were administered orally via oral gavage while Doxil was administered intravenously via tail injection. Body weights and tumor measurements were collected twice weekly. Tumor width and length were measured in millimeters and converted to tumor weight (in milligrams) using the formula (width×Length/2)=tumor weight (mg.). Group 6 and Group 7 showed improved efficacy over Group 5 with Doxil as a single agent (See FIG. 1).

TABLES

TABLE 1

$IC_{50}$ of example compounds in SKOV3 cells and A2780 cells ($IC_{50}$ in μM)

| ID | SKOV3 | A2780 |
|---|---|---|
| 1 | 4.8 | ND |
| 2 | 3.5 | ND |
| 3 | 6.9 | 21 |
| 4 | 2.9 | 0.10 |
| 5 | 2.2 | 3.7 |
| 6 | 0.25 | 0.96 |
| 7 | 2.0 | 2.0 |
| 8 | 1.3 | 1.7 |
| 9 |  | 1.9 |
| 10 | 6.9 | 4.1 |
| 11 | 34 | 40 |
| 12 | 0.7 | 1.4 |
| 13 | 1.9 | 5.1 |
| 14 | 0.3 | 1.1 |
| 15 | 48 | 16 |

TABLE 1-continued

IC$_{50}$ of example compounds in SKOV3 cells
and A2780 cells (IC$_{50}$ in μM)

| ID | SKOV3 | A2780 |
|----|-------|-------|
| 16 | 4.3 | 15 |
| 17 | 8.2 | ND |
| 18 | 21 | ND |
| 19 | 8.1 | ND |
| 20 | 5.8 | ND |
| 21 | 17.7 | 12.1 |
| 22 | 17.6 | 12.1 |
| 23 | 16 | 22 |

We claim:

1. A compound of formula:

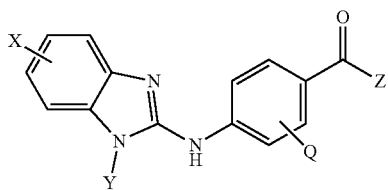

wherein X is selected from the group consisting of H, halo, —C$_1$-C$_6$ alkyl, aryl, —C$_3$-C$_7$ cycloalkyl, and -3-to 10-membered heterocycle;

wherein Y is selected from the group consisting of H, —C$_1$-C$_6$ alkyl, —C$_3$-C$_7$ cycloalkyl, and —C$_1$-C$_6$ alkyl substituted with O—(C$_1$-C$_6$ alkyl);

wherein Z is selected from the group consisting of: NHOH,
and phenylene diamine group (II) of structure

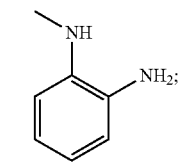

and wherein Q is selected from the group consisting of H, F and Cl;

or a pharmaceutically acceptable salt or solvate thereof.

2. The compound of claim 1, wherein Z is —NHOH.
3. The compound of claim 2, wherein Q is H.
4. The compound of claim 3, wherein X is H.
5. The compound of claim 3, wherein X is Br or F.
6. The compound of claim 1, wherein Z is phenylene diamine group (II) of structure

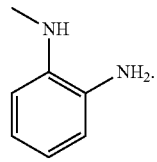

7. The compound of claim 6, wherein Q is H.
8. The compound of claim 7, wherein X is H.
9. The compound of claim 7, wherein X is Br or F.
10. A method of synthesizing a pharmaceutical compound of formula 5 or formula 7, the method comprising:

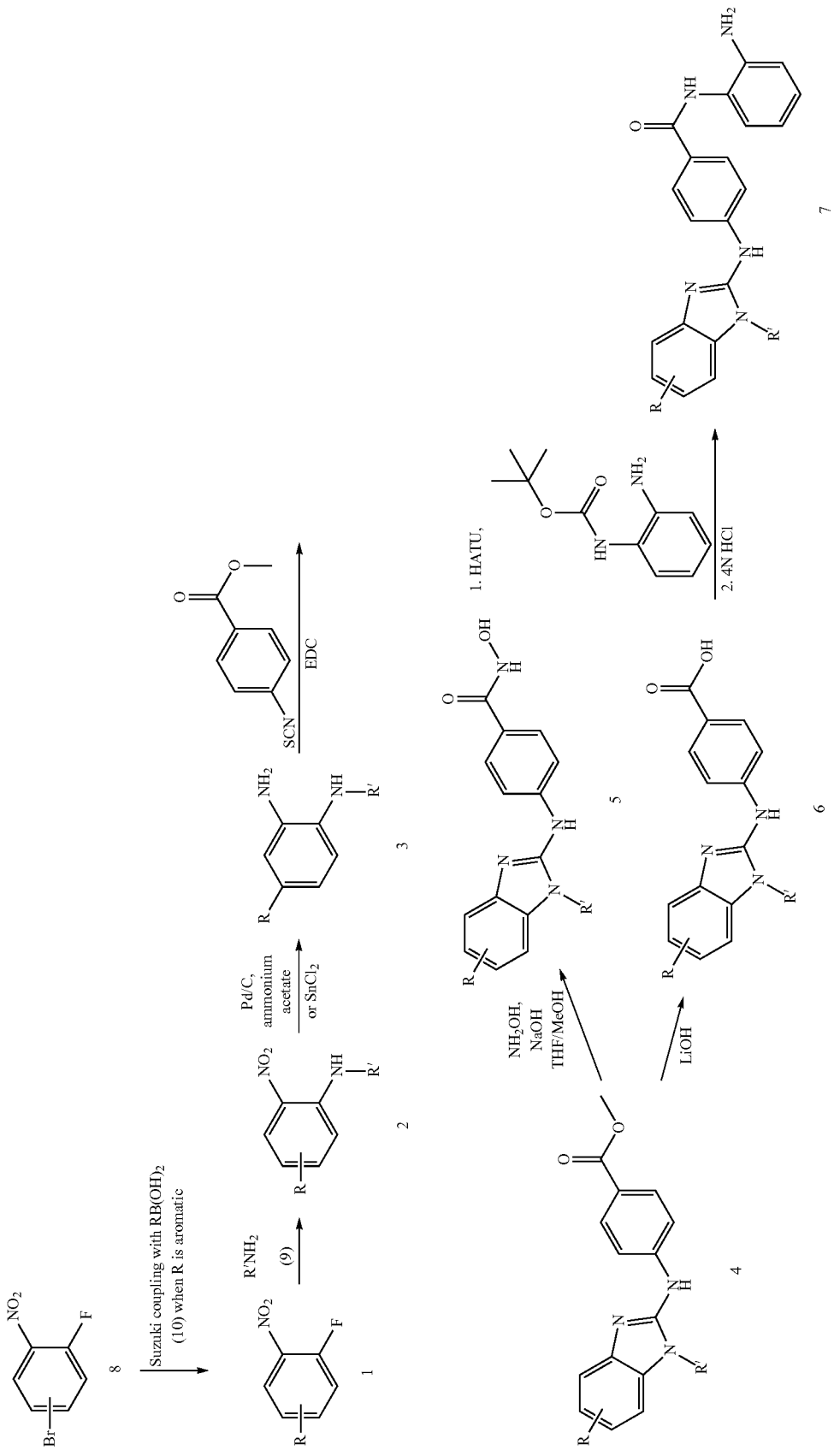

wherein

R is selected from the group consisting of H, halo, —$C_1$-$C_6$ alkyl, aryl, —$C_3$-$C_7$ cycloalkyl, and -3-to 10-membered heterocycle, wherein the —$C_1$-$C_6$ alkyl, aryl, —$C_3$-$C_7$ cycloalkyl, and -3- to 10-membered heterocycle may be unsubstituted or substituted;

R' is 2-isopropoxyethyl, cyclopropylmethyl, cyclobutylmethyl, cyclopentylmethyl, cyclohexylmethyl or cycloheptylmethyl;

compound 9 is selected from the group consisting of 2-isopropoxyethanamine, cyclopropylmethylamine, cyclobutylmethylamine, cyclopentylmethylamine, cyclohexylmethylamine, and cycloheptylmethylamine;

with the proviso that only when R is an aromatic ring is the 2-fluoronitrobenzene of formula 1 prepared from the corresponding bromide of formula 8 through a Suzuki cross coupling reaction.

11. The method of claim 10, wherein compound 9 is 2-isopropoxyethanamine.

12. The method of claim 10, wherein compound 1 is 1-fluoro-2-nitrobenzene or 4-bromo-1-fluoro-2-nitrobenzene.

13. The method of claim 12, wherein compound 9 is cyclopropylmethylamine.

14. The method of claim 12, wherein compound 9 is cyclobutymethylamine.

15. The method of claim 12, wherein compound 9 is cyclopentylmethylamine.

16. The method of claim 12, wherein compound 9 is cyclohexylmethylamine.

17. The method of claim 12, wherein compound 9 is cycloheptylmethylamine.

\* \* \* \* \*